United States Patent
Hardy, Jr. et al.

(10) Patent No.: US 6,866,041 B2
(45) Date of Patent: Mar. 15, 2005

(54) OXYGEN CONCENTRATING AROMA MIXING BREATHABLE AIR DELIVERY APPARATUS AND METHOD

(75) Inventors: Duard I. Hardy, Jr., Miami, FL (US); Thierry de Beaurepaire, Miami, FL (US)

(73) Assignee: Evolution, Inc., Miami, FL (US)

( * ) Notice: Subject to any disclaimer, the term of this patent is extended or adjusted under 35 U.S.C. 154(b) by 0 days.

(21) Appl. No.: 10/146,375

(22) Filed: May 14, 2002

(65) Prior Publication Data

US 2003/0213487 A1 Nov. 20, 2003

(51) Int. Cl.⁷ .............................................. A61M 16/00
(52) U.S. Cl. ............................ 128/204.18; 128/204.22
(58) Field of Search .................. 128/200.24, 200.11, 128/200.14, 201.25, 201.26, 202.21, 203.12, 203.16, 203.17, 203.26, 203.27, 203.29, 204.12, 204.13, 204.18, 204.21, 204.22, 205.11, 205.12; 131/194, 195, 198, 200, 330, 329, 214, 215.1, 215.2, 215.3

(56) References Cited

U.S. PATENT DOCUMENTS

| | | | | |
|---|---|---|---|---|
| 4,302,224 A | * | 11/1981 | McCombs et al. ............. | 96/109 |
| 4,561,287 A | * | 12/1985 | Rowland ....................... | 95/11 |
| 4,597,781 A | * | 7/1986 | Spector ......................... | 96/52 |
| 5,553,607 A | * | 9/1996 | Chiu et al. ............. | 128/203.26 |
| 5,827,358 A | * | 10/1998 | Kulish et al. .................. | 96/115 |
| 6,250,301 B1 | * | 6/2001 | Pate ...................... | 128/203.26 |
| 6,354,301 B2 | * | 3/2002 | McCoy ....................... | 131/194 |
| 6,447,816 B1 | * | 9/2002 | Vail et al. .................... | 424/742 |
| 6,481,437 B1 | * | 11/2002 | Pate ...................... | 128/203.26 |
| 6,513,524 B1 | * | 2/2003 | Storz ..................... | 128/203.26 |
| 6,536,431 B1 | * | 3/2003 | Simler ................... | 128/205.12 |
| 6,561,188 B1 | * | 5/2003 | Ellis ..................... | 128/206.11 |
| 2003/0150451 A1 | * | 8/2003 | Shayan ................. | 128/203.12 |

* cited by examiner

Primary Examiner—Henry Bennett
Assistant Examiner—Teena Mitchell
(74) Attorney, Agent, or Firm—Frank L. Kubler

(57) ABSTRACT

An apparatus for concentrating the oxygen content of and injecting aroma into a stream of air and delivering the stream of air to the nostrils of a person includes an air intake filter in fluid communication with the air compressor for drawing a stream of air out of the surrounding atmosphere; a sieve bed in fluid communication with the air intake means, each sieve bed containing a quantity of nitrogen absorption material and having sieve bed input and output valve mechanism; so that the sieve bed extracts nitrogen from the air stream so that the proportion of oxygen exiting the sieve bed is elevated, and as the input valve mechanism closes, the sieve bed output valve mechanism opens and vents absorbed nitrogen from the sieve bed to the atmosphere; an aroma chamber containing aroma releasing material in fluid communication with the output valve mechanism.

13 Claims, 7 Drawing Sheets

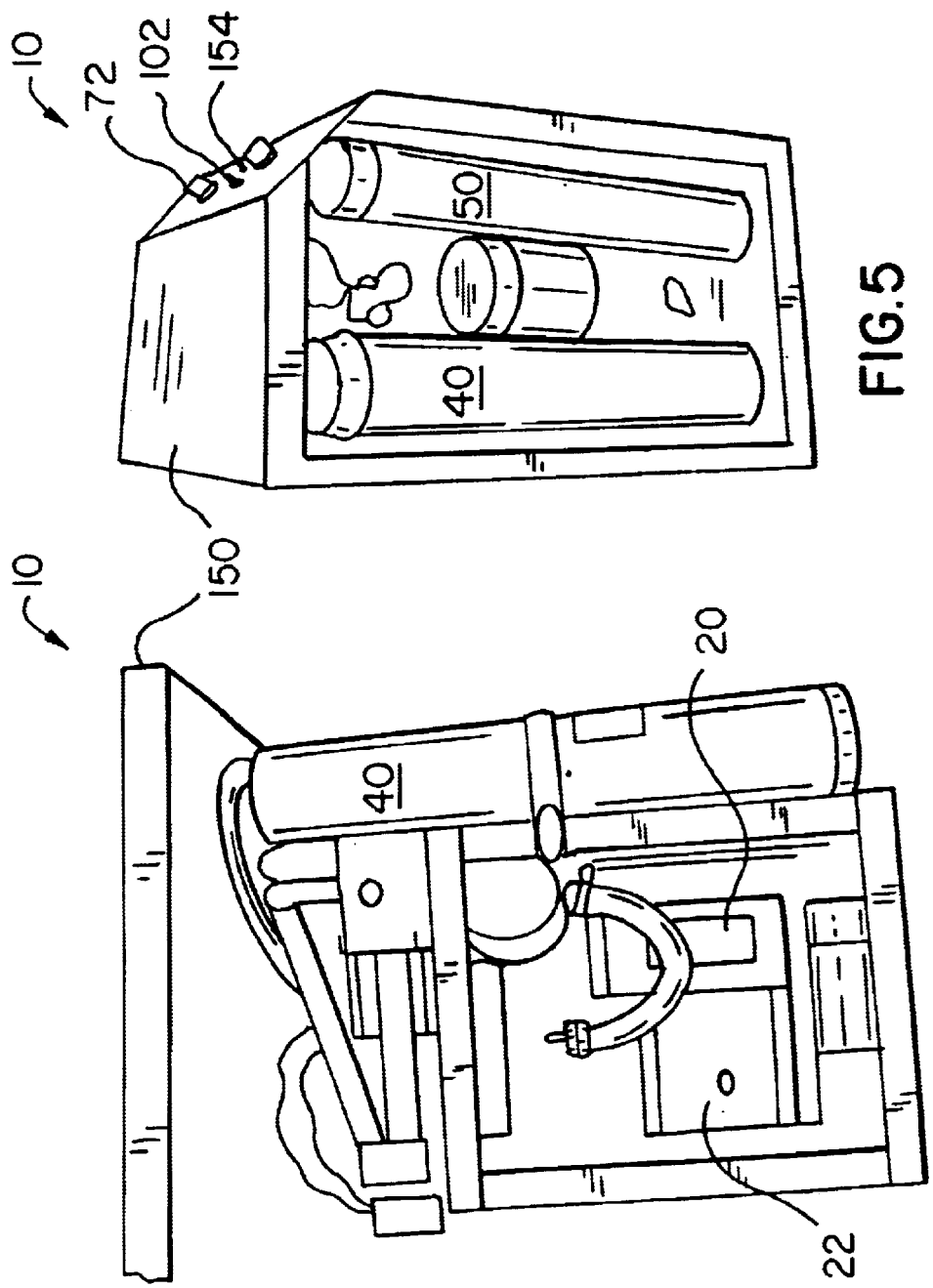

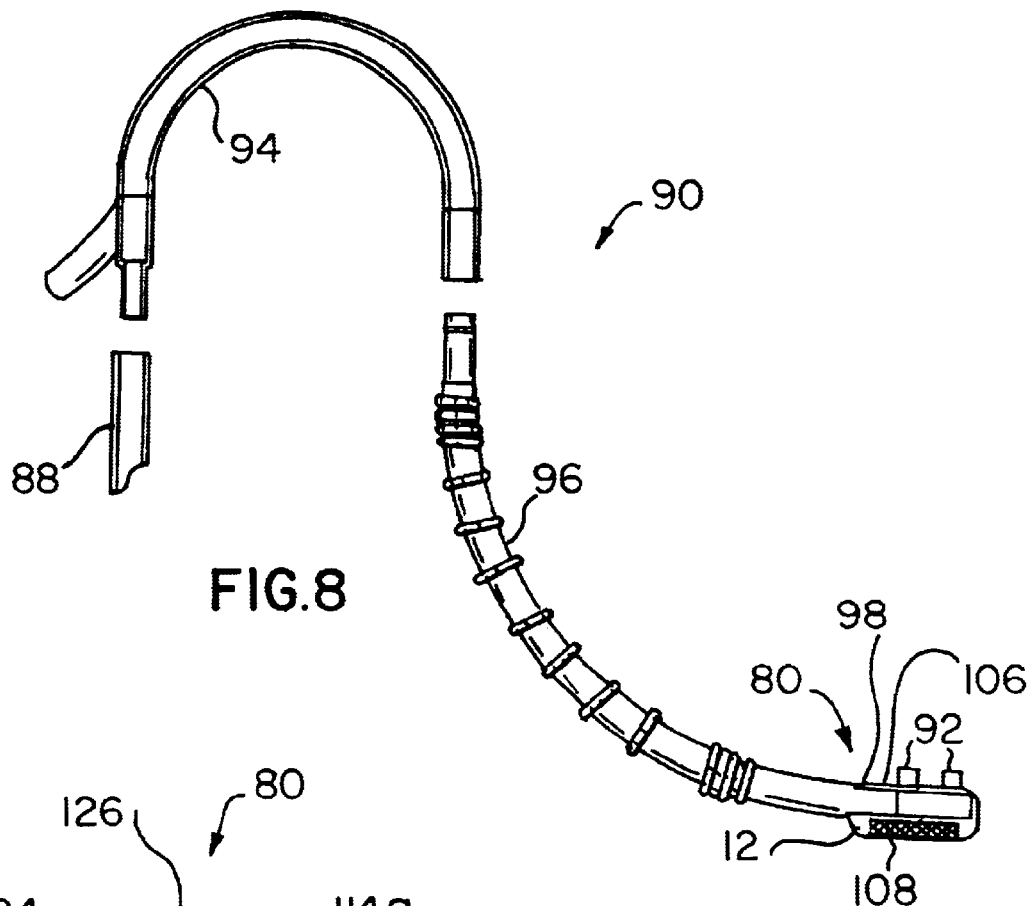
FIG. 8
FIG. 9
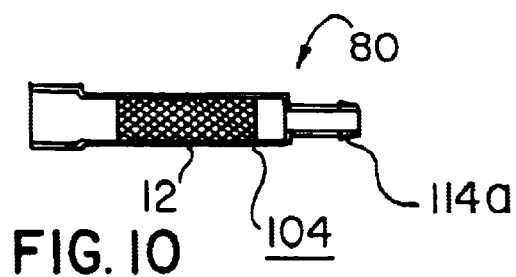
FIG. 10

OXYGEN CONCENTRATING AROMA MIXING BREATHABLE AIR DELIVERY APPARATUS AND METHOD

BACKGROUND OF THE INVENTION

1. Field of the Invention

The present invention relates generally to the field of breathing devices which deliver breathable gases to a user. More specifically the present invention relates to an apparatus for concentrating the oxygen content of and injecting aroma or homeopathic medication into a stream of air and delivering the stream of air to the nostrils of a person using the apparatus. The apparatus includes an air compressor driven by a compressor motor, an air intake filter which draws a stream of air out of the surrounding atmosphere and delivers the stream of air into the air compressor which compresses the air, and directs the compressed air to the first and second sieve beds each containing a quantity of nitrogen absorption material, a Y-pipe with sieve input valve means and sieve output valve means, an apparatus circuit including a cycle timer and valve switching means operationally connected to the cycle timer and to the sieve input valve means, alternately delivering the stream of air from the compressor into the first sieve bed and into the second sieve bed, each of which extract nitrogen from the air stream so that the proportion of oxygen exiting the sieve beds is elevated to a preferred level of 40 to 80 percent at approximately 5 psig, and as the input valve of each sieve closes, sieve output valve means of that sieve opens and vents absorbed nitrogen to the atmosphere, then the stream of air advancing from the sieve bed into an inventive aroma chamber containing aroma releasing material and through a canula to exit ports with nose delivery nozzles. The oxygen concentration is maintained below medical application levels by delivering the air stream through the sieve beds at a rate above the design parameters of the sieve beds, so that the nitrogen absorption material in the sieve beds is oversaturated with nitrogen, decreasing the proportionality of the oxygen gas in the output to a concentration between 40% and 65%.

2. Description of the Prior Art

There have long been oxygen concentrating devices for increasing the proportion of oxygen in breathable air, either for medical or recreational purposes, or for mood enhancement. Other unrelated devices have delivered selected aromas to users for mood enhancement. A problem with these previously separate and distinct therapies has been that simultaneous delivery and the resulting synergistic, mutually beneficial effect has not been provided.

It is thus an object of the present invention to provide an apparatus for delivering air with concentrated oxygen and containing an aroma to a person using the apparatus, and which additionally optionally delivers music or other suitable sound, or delivers video or other viewing matter, into the person.

It is another object of the present invention to provide such an apparatus which is compact and efficient.

It is still another object of the present invention to provide such an apparatus which is light weight and portable.

It is finally an object of the present invention to provide such an apparatus which is inexpensive to manufacture.

SUMMARY OF THE INVENTION

The present invention accomplishes the above-stated objectives, as well as others, as may be determined by a fair reading and interpretation of the entire specification.

An apparatus is provided for concentrating the oxygen content of and injecting aroma into a stream of air and delivering the stream of air to the nostrils of a person, the apparatus including an air compressor and a compressor motor drivably connected to the air compressor; an air intake filter in fluid communication with the air compressor for drawing a stream of air out of the atmosphere surrounding the apparatus and delivering the stream of air into the air compressor for compressing the air; first and second sieve beds in fluid communication with the air compressor, each sieve bed containing a quantity of nitrogen absorption material; a sieve input valve mechanism and a sieve output valve mechanism in fluid communication with each of the first and second sieve beds; a cycle timer connected to the sieve input valve mechanism and to the sieve output valve mechanism; and a valve switching device connected to the cycle timer and to the sieve input valve mechanism, alternately delivering the stream of air into the first sieve bed and into the second sieve bed; so that each of the first and second sieve beds extracts nitrogen from the air stream, so that the proportion of oxygen in the air stream exiting the sieve beds is elevated, and as the input valve closes for each sieve bed, the sieve bed output valve mechanism of the sieve bed opens and vents nitrogen to the atmosphere; an aroma chamber containing aroma releasing material in fluid communication with the first and second sieve beds, so that the stream of air is delivered through the aroma chamber and receives and retains an aroma; and a canula in fluid communication with the aroma chamber and comprising an exit port with a nose delivery nozzle.

The apparatus preferably additionally includes an outer housing with a air stream nipple in fluid communication with the sieve beds, where the aroma chamber is connected to the air stream nipple. The aroma chamber preferably includes a chamber tube having a tube first end fitted sealingly around the air stream nipple and having a tube second end, and includes a diffuser adaptor fitted into and secured within the tube second end, the diffuser adaptor including a mass of air passing filter material, which preferably functions as a sanitary device, fitted into the chamber tube and impregnated with the aroma producing material, and including a chamber nozzle having a diameter smaller than that of the chamber tube with a radial circular flange secured within the chamber tube, and oriented such that the chamber nozzle protrudes outwardly from the tube second end. The aroma chamber preferably includes a mounting tube segment sized to fit snugly onto air stream nipple, a first radial flange expanding to a wider compartment tube segment, and a second radial flange converging to a narrower chamber nozzle, where the compartment tube segment contains a mass of air passing filter material impregnated with the aroma producing material.

The aroma chamber preferably includes tube structure configured to fit to the air stream nipple, where the tube structure contains the aroma producing material. The canula preferably includes a first flexible mounting segment, an ear engaging segment adapted in shape to fit on the human head and a second flexible segment extending from the ear engaging segment and a detachable nasal tip with air passages. The flexible segment optionally includes a lateral protrusion containing an aroma producing substance.

The nitrogen absorption material preferably includes Zeolite. The apparatus additionally includes an apparatus electric circuit, the electrical circuit including an activation switch connected to a delivery duration timer adjustable to a selected treatment duration. The apparatus preferably additionally includes a flow control valve in fluid communication with the first and second sieve beds and with the air stream nozzle, permitting selection of an air stream flow rate.

An apparatus is further provided for concentrating the oxygen content of and injecting aroma into a stream of air and delivering the stream of air to the nostrils of a person, including an air intake filter in fluid communication with the air compressor for drawing a stream of air out of the surrounding atmosphere; a sieve bed in fluid communication with the air intake filter, each sieve bed containing a quantity of nitrogen absorption material and having sieve bed input and output valve mechanism; so that the sieve bed extracts nitrogen from the air stream so that the proportion of oxygen exiting the sieve bed is elevated, and as the input valve mechanism closes, the sieve bed output valve mechanism opens and vents absorbed nitrogen from the sieve bed to the atmosphere; an aroma chamber containing aroma releasing material in fluid communication with the output valve mechanism so that the stream of air is delivered through the aroma chamber and receives and retains an aroma; and a canula comprising an exit port having a nose delivery nozzle.

A method of delivering air to a person is also provided, including the steps of: creating an air stream, compressing the air in the air stream; extracting a portion of the nitrogen from air within the air stream; delivering aroma material into the air stream; and delivering the air stream to the nostrils of a person.

BRIEF DESCRIPTION OF THE DRAWINGS

Various other objects, advantages, and features of the invention will become apparent to those skilled in the art from the following discussion taken in conjunction with the following drawings, in which:

FIG. 4 is rear view of the apparatus with the housing removed to reveal several interior elements.

FIG. 5 is side view of the apparatus with the housing removed to reveal sieve beds.

FIG. 8 is a side view of a preferred canula, shown in partial cross-section, in which the aroma producing material is contained within a lateral chamber adjacent the nose delivery nasal tips.

FIG. 9 is a cross-sectional side view of an alternative aroma chamber containing a disk of aroma producing material.

FIG. 10 is a cross-sectional side view of a further alternative aroma chamber containing a cylinder of aroma producing material.

DETAILED DESCRIPTION OF THE PREFERRED EMBODIMENTS

Figure 1:
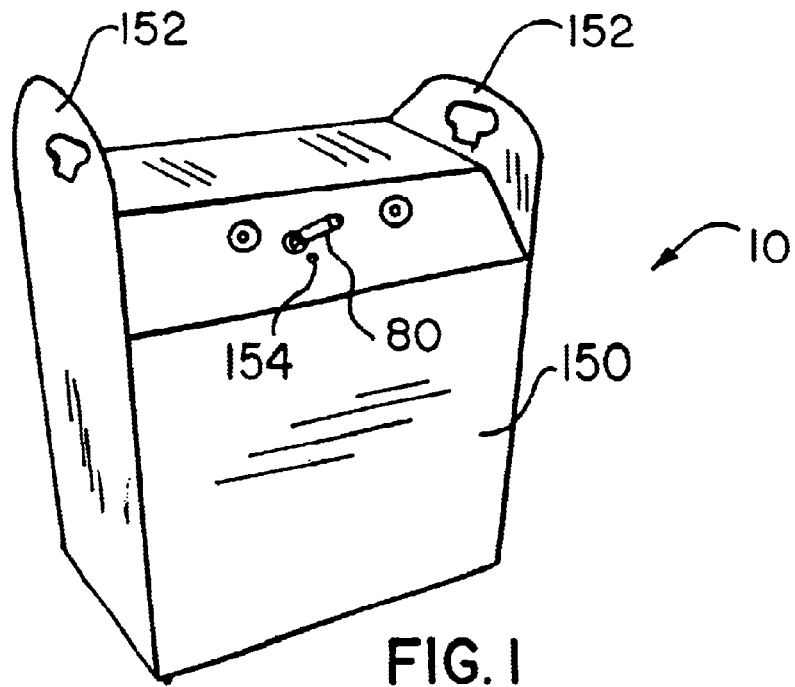
FIG. 1 is a front perspective view of the preferred embodiment of the apparatus, showing housing handles and the releasibly fitted aroma chamber for connection to a cannula.
Figure 2:
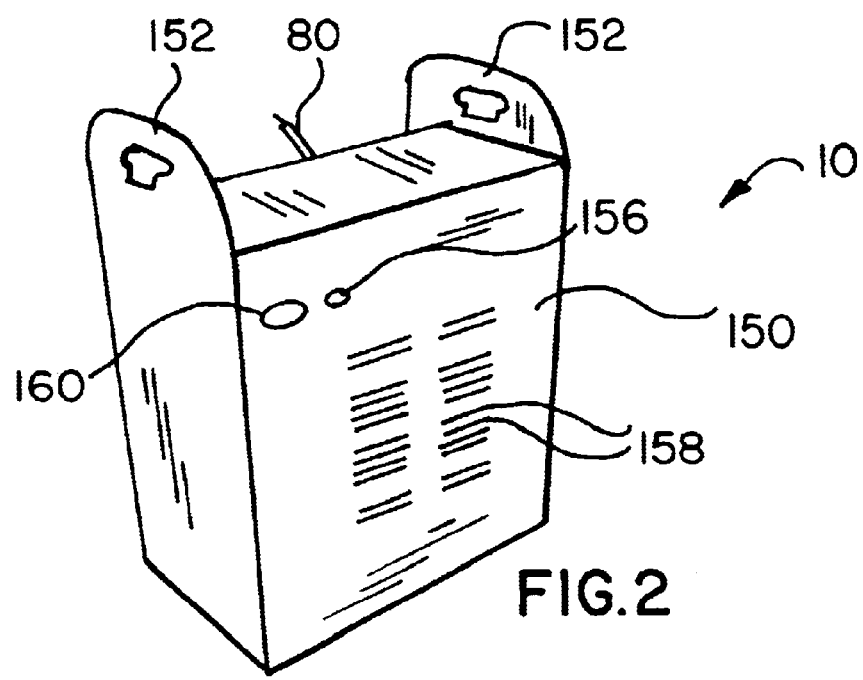
FIG. 2 is a rear perspective view of the preferred embodiment of the apparatus, showing cooling louvers in the housing rear wall.

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Reference is now made to the drawings, wherein like characteristics and features of the present invention shown in the various FIGURES are designated by the same reference numerals.

First Preferred Embodiment

Figure 3:
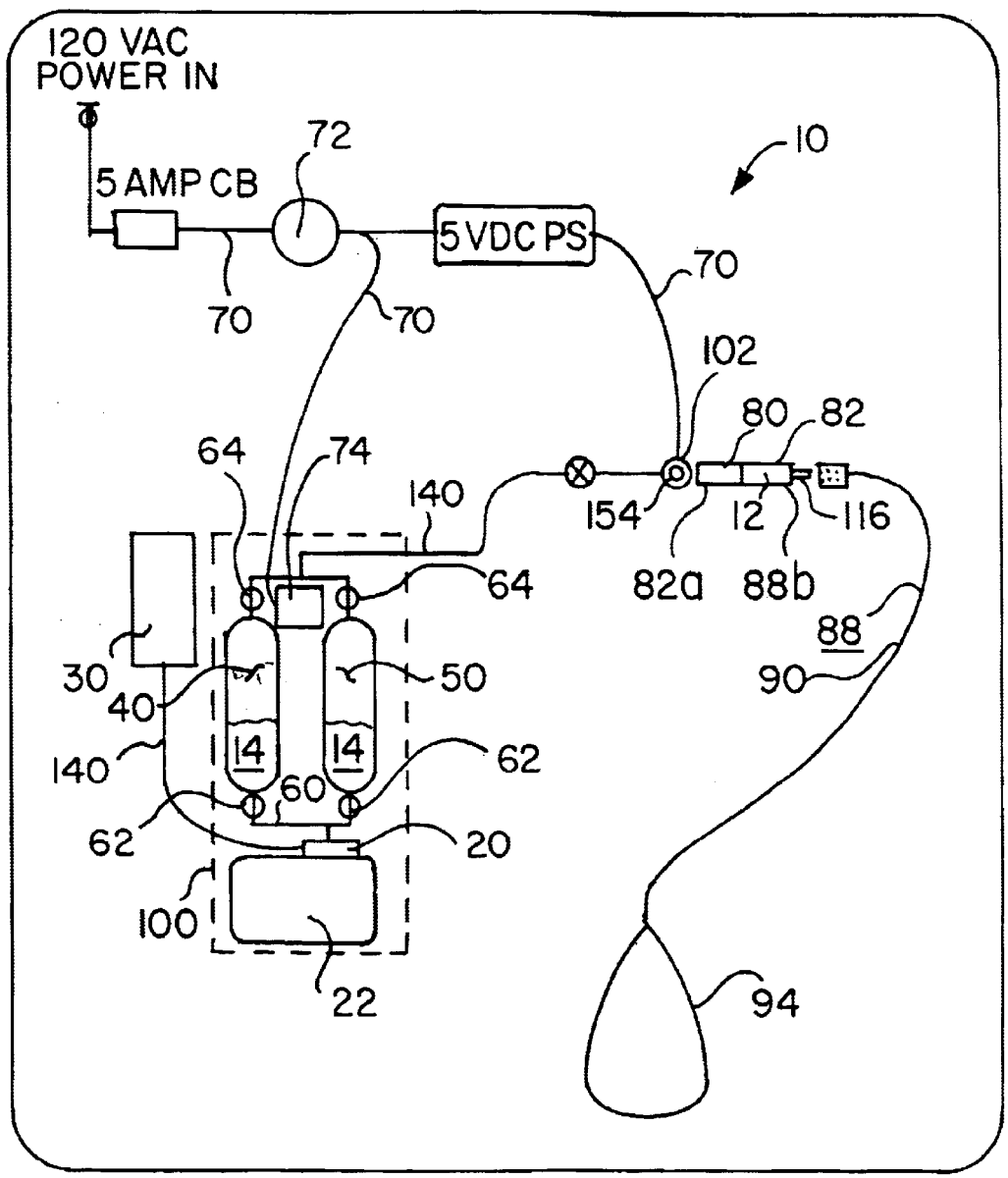
FIG. 3 is a schematic showing the various elements of the apparatus and their interrelationships.
Figure 6:
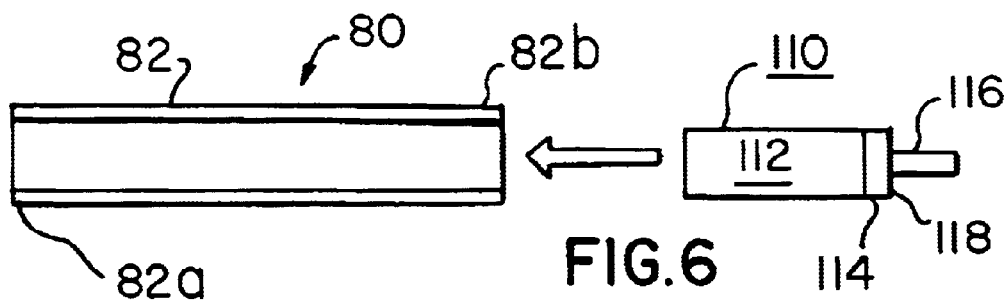
Figure 7:
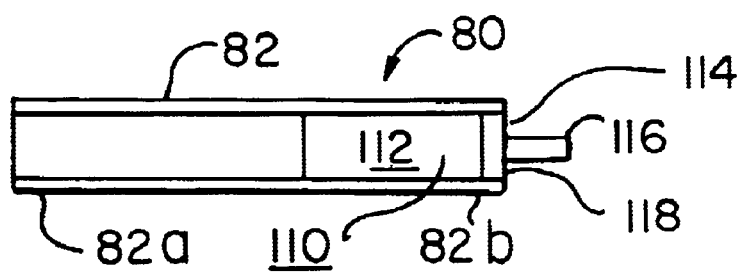
FIG. 7 includes a cross-sectional side view of an aroma chamber in exploded relation to the filter cylinder, and includes a side view of an assembled aroma chamber containing the filter cylinder.

Referring to FIGS. 1–14, an apparatus 10 is disclosed for concentrating the oxygen content of and injecting gaseous or particulate aroma material 12 or homeopathic or other medication into a stream of air and delivering the stream of air to the nostrils of a person using the apparatus 10. Apparatus 10 includes an air compressor 20 driven by a compressor motor 22, an air intake filter 30 which draws a stream of air out of the surrounding atmosphere and delivers the stream of air into the air compressor 20 which compresses the air, first and second sieve beds 40 and 50 each containing a quantity of nitrogen absorption material 14, a Y-pipe manifold 60 with sieve input valve means 62 and sieve output valve means 64, an apparatus circuit 70 including a cycle timer 72 and valve switching means 74 operationally connected to the cycle timer 72 and to the sieve input valve means 62, alternately delivering the stream of air from air compressor 20 into the first sieve bed 40 and into the second sieve bed 50, each of which extract nitrogen from the air stream so that the proportion of oxygen exiting sieve beds 40 and 50 is elevated to a desired level lower than the 90 percent minimum used for medical applications such as of 40 to 80 percent at 5 psig, and as the input valve of each sieve bed 40 and 50 closes, sieve output valve means 64 of that sieve bed opens and vents absorbed nitrogen to the atmosphere, then the stream of air is delivered through an aroma chamber 80 containing aroma releasing material 12 and through a canula 90 to exit ports with nose delivery nasal tips 92. See FIGS. 3 and 14.

The oxygen concentration in the air stream is maintained below medical application levels by delivering the air stream through the sieve beds 40 and 50 at a rate above the design parameters of the sieve beds, so that the nitrogen absorption material 14 in sieve beds 40 and 50 approaches the nitrogen saturation level and becomes less efficient, so that the air stream retains some of its nitrogen. Apparatus 10 has an outer apparatus housing 100 with an air stream nipple 102 to which the stream of air is delivered from the sieve beds 40 and 50, and the aroma chamber 80 is connected to the nipple 102.

One embodiment of the inventive aroma chamber 80 includes a segment of chamber tube 82, formed of acrylic or any other suitable material, having a tube first end 82a which fits snugly and sealingly around the air stream nipple 102 and a tube second end 82b and into which a diffuser adaptor 110 is fitted and secured with glue or any other suitable bonding substance. In this instance the diffuser adaptor 110 includes a filter cylinder 112 of air passing filter material sized to fit snugly into chamber tube 82 and impregnated with an aroma producing material 12 which preferably is an oil of any of a variety of scents, and a chamber end structure 114 including a chamber nozzle 116 having a diameter smaller than that of chamber tube 82 and a radial circular flange 118 sized to fit snugly into chamber tube 82, the filter cylinder 112 being fitted into chamber tube second end 82b and the circular flange 118 being radially coated with adhesive and being inserted into tube second end 82b of chamber tube 82, with chamber nozzle 116 protruding outwardly from the end of chamber tube 82. See FIGS. 6 and 7. The chamber nozzle 116 preferably has hose barbs 114a around its tip and a flexible cannula 90, described in detail below, fits snugly onto chamber nozzle 116.

An alternative version of aroma chamber 80 includes a first mounting tube segment 122 sized to fit snugly onto air stream nipple 102, a first radial flange 124 expanding to a wider compartment tube segment 126, a second radial flange 128 converging to a narrower chamber nozzle 116 as above described. See FIG. 9. The compartment tube segment 126 contains a filter material disk 132 impregnated with an aroma material 12. A version of aroma chamber 80 having a unified tubular body is shown in FIG. 10.

Figure 13:
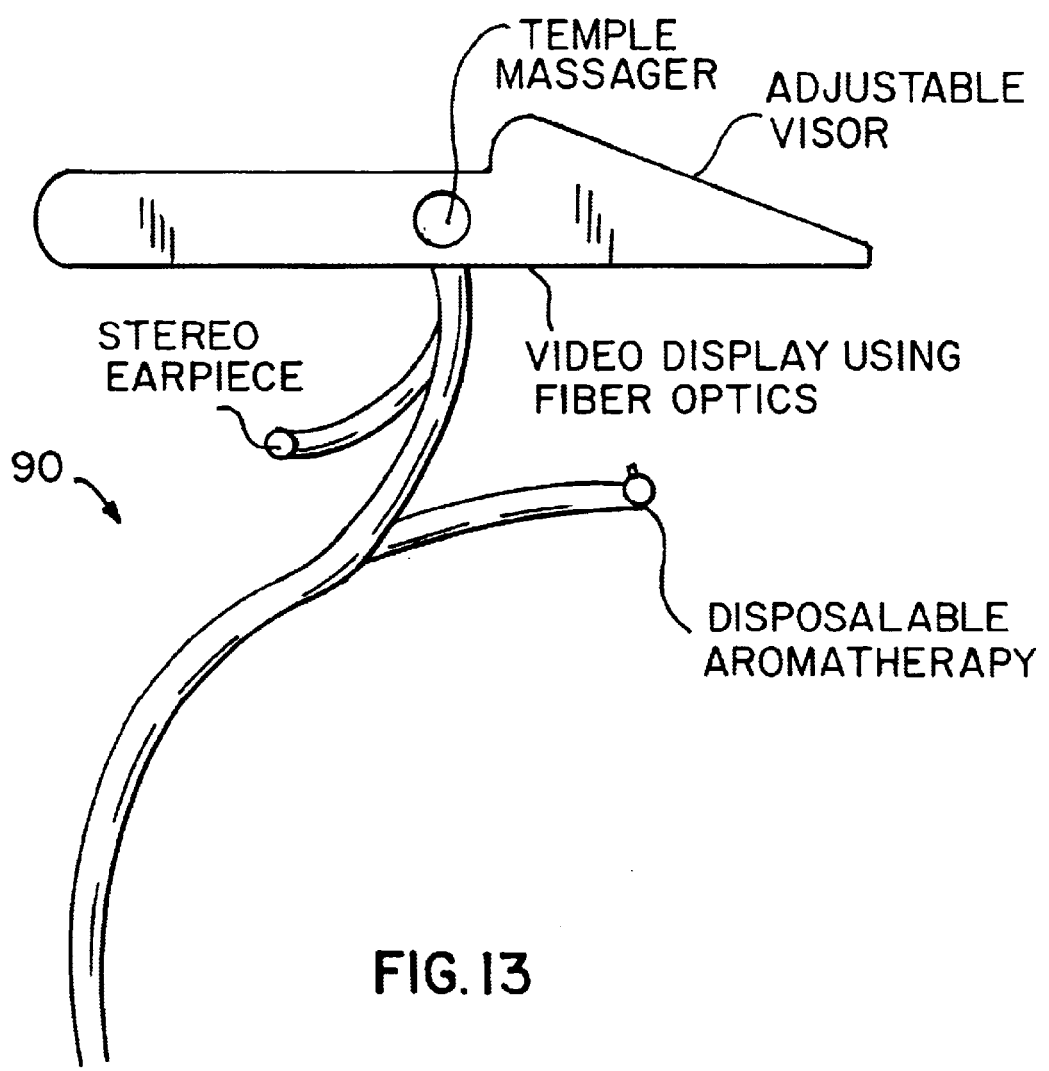
FIG. 13 is a side schematic view of an alternative canula containing audio and video delivery means.
Figure 14:
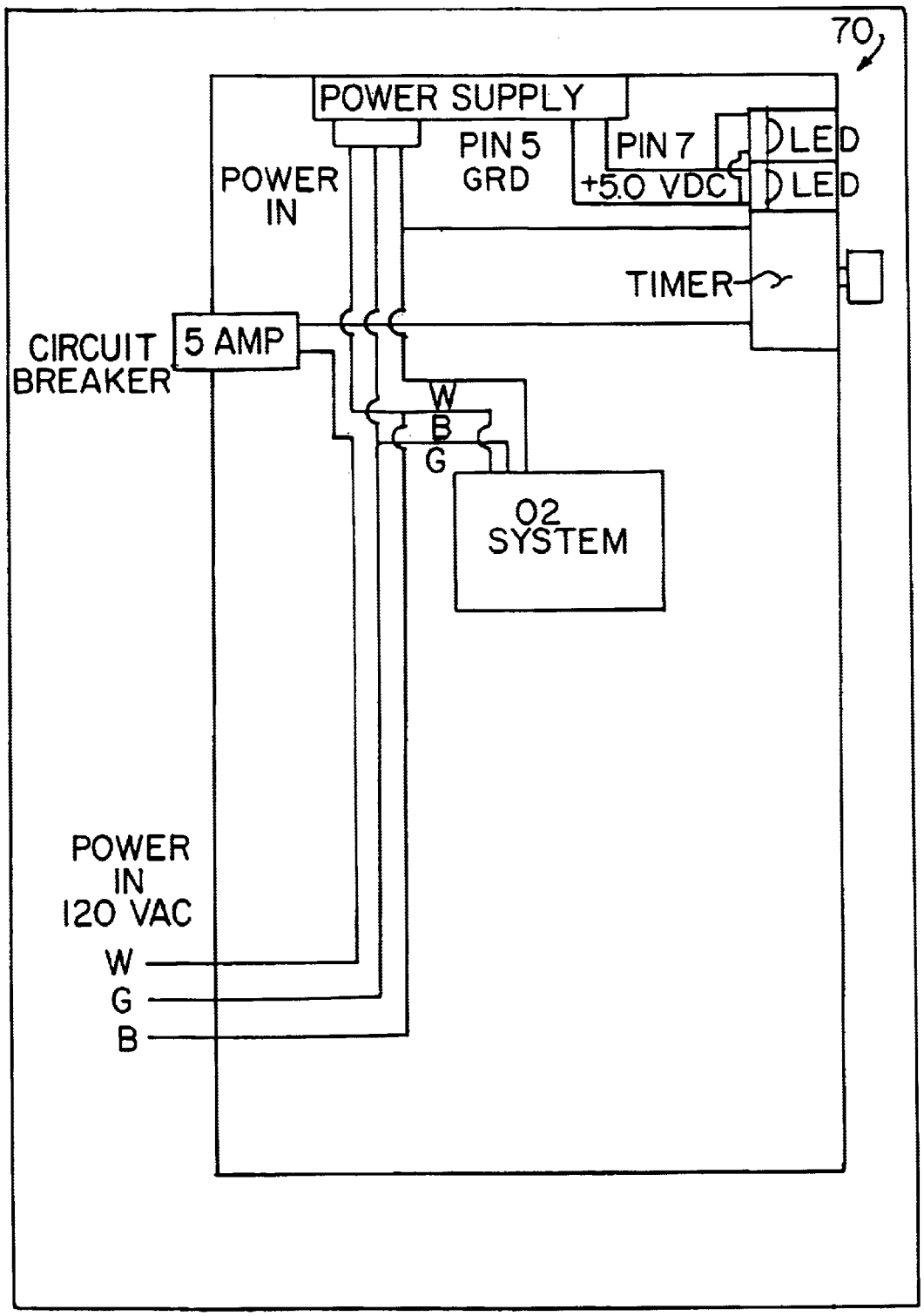
FIG. 14 is a preferred wiring diagram of the apparatus.

The preferred canula 90 includes a first flexible cannula tube 88, a semi-flexible and curved ear engaging segment 94 and a second flexible segment 96 extending from the ear engaging segment 94 and a detachable and disposable nasal tip 98 with air passages. As yet another alternative aroma chamber design, an aroma impregnated pad 104 is placed in a lateral protrusion chamber 106 formed as part of nasal tip 98. See FIGS. 8, 11 and 12. A version of cannula 90 combined with sound generating and delivery means is illustrated in FIG. 13.

Figures 11, 12:
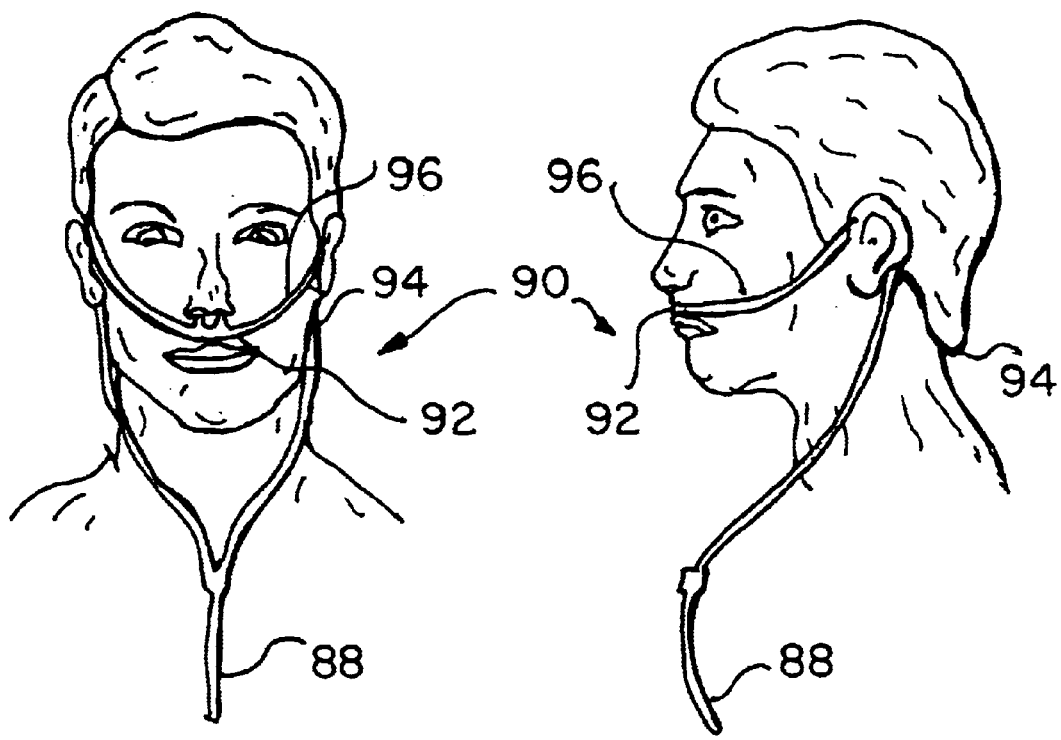
FIGS. 11 and 12 are front and side views, respectively, of a human head fitted with the preferred canula.

The preferred nitrogen absorption material 14 is Zeolite. The apparatus electric circuit 70 includes an activation switch 72 and preferably includes a delivery duration timer 74 which is adjustable with a dial 74a to a desired treatment duration, but otherwise preferably is set for 60 minutes. Apparatus 10 preferably includes a flow control valve 76 between the sieve beds 40 and 50 and the air stream nipple 102 which permits air stream flow rate adjustment to suit the needs of a given user. Electric circuit 70 also includes a valve control module 78 of conventional design which controls the operation of the sieve bed input and output valves 62 and 64, respectively, and a strobe light 154 mounted to the apparatus housing 150 adjacent to the air stream nipple 102. Apparatus housing 150 preferably includes carrying handles 152. Air intake filter 30 preferably is connected to an air intake tube 32. FIG. 12 also shows an elapsed time meter 160 showing the length of time a single use has progressed, a circuit breaker 158 and housing ventilation louvers 156. Air stream conduit 140 preferably interconnects the various elements through which the air stream passes. Examples of homeopathic medications delivered into the air stream are those produced by BE WELL HOMEOPATHICS™ including "be Well Allergy", "Be Well Arnica Plus", and "Be Well Lungs".

Method

In practicing the invention, the following method may be used. The method includes the steps of creating an air stream, compressing the air in the air stream; extracting a portion of the nitrogen from air within the air stream; delivering aroma material into the air stream; and delivering the air stream to the nostrils of a person.

While the invention has been described, disclosed, illustrated and shown in various terms or certain embodiments or modifications which it has assumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. An apparatus for concentrating the oxygen content of and injecting aroma into a stream of air and adapted to deliver a stream of air to nostrils of a person, comprising:

an air compressor and a compressor motor drivably connected to said air compressor for drawing a stream of air out of the atmosphere surrounding the apparatus;

first and second sieve beds in fluid communication with said air compressor, each said sieve bed containing a quantity of nitrogen absorption material;

sieve input valve means and sieve output valve means in fluid communication with each of said first and second sieve beds and having an air stream nipple;

a cycle timer connected to sieve input valve means and to said sieve output valve means;

and valve switching means connected to said cycle timer and to said sieve input valve means, alternately delivering the stream of air into said first sieve bed and into said second sieve bed;

such that each of said first and second sieve beds extracts nitrogen from the air stream, such that the proportion of oxygen in the air stream exiting said sieve beds is elevated, and as said input valve closes for each said sieve bed, sieve bed output valve means of each said sieve bed opens and vents nitrogen to the atmosphere;

an aroma chamber containing aroma releasing material in fluid communication with said first and second sieve beds, such that the stream of air is delivered through said aroma chamber and receives and retains an aroma, said aroma chamber comprising a chamber tube having a tube first end fitted sealingly around said air stream nipple and having a tube second end, and comprising a diffuser adaptor fitted into and secured within said tube second end, said diffuser adaptor comprising a mass of air passing filter material fitted into said chamber tube and impregnated with the aroma releasing material, and comprising a chamber nozzle having a diameter smaller than that of said chamber tube with a radial circular flange secured within said chamber tube, and oriented such that said chamber nozzle protrudes outwardly from said tube second end;

and a canula in fluid communication with said aroma chamber with said aroma chamber and comprising an exit port with a nose delivery nozzle.

2. The apparatus of claim 1, wherein said aroma chamber comprises a mounting tube segment sized to fit snugly onto said air stream nipple, a first radial flange expanding to a wider compartment tube segment, and a second radial flange converging to a narrower chamber nozzle, wherein said compartment tube segment contains a mass of air passing filter material impregnated with said aroma releasing material.

3. The apparatus of claim 1, wherein said aroma chamber comprises tube means configured to fit to said air stream nipple, wherein said tube means contains said aroma releasing material.

4. The apparatus of claim 1, additionally comprising a flow control valve in fluid communication with said first and second sieve beds and with said nose delivery nozzle, permitting selection of an air stream flow rate.

5. An apparatus for concentrating the oxygen content of and injecting aroma into a stream of air and adapted to deliver a stream of air to nostrils of a person, comprising:

an air compressor and a compressor motor drivably connected to said air compressor for drawing a stream of air out of the atmosphere surrounding the apparatus;

first and second sieve beds in fluid communication with said air compressor, each said sieve bed containing a quantity of nitrogen absorption material;

sieve input valve means and sieve output valve means in fluid communication with each of said first and second sieve beds and having an air stream nipple;

a cycle timer connected to sieve input valve means and to said sieve output valve means;

and valve switching means connected to said cycle timer and to said sieve input valve means, alternately delivering the stream of air into said first sieve bed and into said second sieve bed;

such that each of said first and second sieve beds extracts nitrogen from the air stream, such that the proportion of oxygen in the air stream exiting said sieve beds is elevated, and as said input valve closes for each said sieve bed, sieve bed output valve means of each said sieve bed opens and vents nitrogen to the atmosphere;

an aroma chamber containing aroma releasing material in fluid communication with said first and second sieve beds, such that the stream of air is delivered through said aroma chamber and receives and retains an aroma;

an outer housing with said air stream nipple in fluid communication with said sieve beds, wherein said aroma chamber is connected to said air stream nipple.

6. An apparatus for concentrating the oxygen content of and injecting aroma into a stream of air and adapted to deliver a stream of air to nostrils of a person, comprising:

an air compressor and a compressor motor drivably connected to said air compressor for drawing a stream of air out of the atmosphere surrounding the apparatus;

first and second sieve beds in fluid communication with said air compressor, each said sieve bed containing a quantity of nitrogen absorption material;

sieve input valve means and sieve output valve means in fluid communication with each of said first and second sieve beds and having an air stream nipple;

a cycle timer connected to sieve input valve means and to said sieve output valve means;

and valve switching means connected to said cycle timer and to said sieve input valve means, alternately delivering the stream of air into said first sieve bed and into said second sieve bed;

such that each of said first and second sieve beds extracts nitrogen from the air stream, such that the proportion of oxygen in the air stream exiting said sieve beds is elevated, and as said input valve closes for each said sieve bed, sieve bed output valve means of each said sieve bed opens and vents nitrogen to the atmosphere;

an aroma chamber containing aroma releasing material in fluid communication with said first and second sieve beds, such that the stream of air is delivered through said aroma chamber and receives and retains an aroma;

and a canula in fluid communication with said aroma chamber with said aroma chamber and comprising an exit port with a nose delivery nozzle;

wherein said canula comprises a first flexible mounting segment, a curved ear engaging segment and a second flexible segment extending from said ear engaging segment and a detachable nasal tip with air passages.

7. The apparatus of claim 6, wherein said second flexible segment comprises a lateral protrusion containing an aroma producing substance.

8. An apparatus for concentrating the oxygen content of and injecting aroma into a stream of air and adapted to deliver a stream of air to nostrils of a person, comprising:

an air compressor and a compressor motor drivably connected to said air compressor for drawing a stream of air out of the atmosphere surrounding the apparatus;

first and second sieve beds in fluid communication with said air compressor, each said sieve bed containing a quantity of nitrogen absorption material;

sieve input valve means and sieve output valve means in fluid communication with each of said first and second sieve beds and having an air stream nipple;

a cycle timer connected to sieve input valve means and to said sieve output valve means;

and valve switching means connected to said cycle timer and to said sieve input valve means, alternately delivering the stream of air into said first sieve bed and into said second sieve bed;

such that each of said first and second sieve beds extracts nitrogen from the air stream, such that the proportion of oxygen in the air stream exiting said sieve beds is elevated, and as said input valve closes for each said sieve bed, sieve bed output valve means of each said sieve bed opens and vents nitrogen to the atmosphere;

an aroma chamber containing aroma releasing material in fluid communication with said first and second sieve beds, such that the stream of air is delivered through said aroma chamber and receives and retains an aroma;

an apparatus electric circuit, said electrical circuit comprising an activation switch connected to a delivery duration timer adjustable to a selected treatment duration.

9. An apparatus for concentrating the oxygen content of and injecting aroma into a stream of air and adapted to deliver a stream of air to nostrils of a person, comprising:

an air pump means for drawing a stream of air out of the surrounding atmosphere;

a sieve bed in fluid communication with said air pump means, said sieve bed containing a quantity of nitrogen absorption material and having sieve bed input and output valve means;

such that said sieve bed extracts nitrogen from the air stream such that the proportion of oxygen exiting said sieve bed is elevated, and as said input valve means closes, said sieve bed output valve means opens and vents absorbed nitrogen from said sieve bed to the atmosphere;

an aroma chamber containing aroma releasing material in fluid communication with said output valve means such that the stream of air is delivered through said aroma chamber and receives and retains an aroma;

and a canula comprising an exit port having a nose delivery nozzle;

and a flow control valve in fluid communication with said sieve bed and with said nose delivery nozzle, permitting selection of an air stream flow rate.

10. A method of delivering air to a person, comprising the steps of: providing first and second sieve beds; creating an air stream, compressing the air in the air stream; selecting an air stream flow rate with flow control valve means in fluid communication with said first and second sieve beds and with an air stream nozzle; extracting a portion of the nitrogen from air within the air stream; delivering aroma material into the air stream; and adapted to deliver a air stream to nostrils of a person.

11. An apparatus for concentrating the oxygen content of and injecting aroma into a stream of air and adapted to deliver a stream of air to nostrils of a person, comprising:

an air pump means for drawing a stream of air out of the surrounding atmosphere;

a sieve bed in fluid communication with said air pump means, said sieve bed containing a quantity of nitrogen absorption material and having sieve bed input and output valve means;

such that said sieve bed extracts nitrogen from the air stream such that the proportion of oxygen exiting said sieve bed is elevated, and as said input valve means closes, said sieve bed output valve means opens and vents absorbed nitrogen from said sieve bed to the atmosphere;

an aroma chamber containing aroma releasing material and comprising a chamber tube having a tube first end in fluid communication with said output valve means and having a tube second end such that the stream of air is delivered through said aroma chamber and receives and retains an aroma, and comprising a diffuser adaptor fitted into and secured within said tube second end, said diffuser adaptor comprising a mass of material fitted into said chamber tube and impregnated with the aroma releasing material;

and a canula comprising an exit port having a nose delivery nozzle.

12. The apparatus of claim 11, additionally comprising a chamber nozzle having a diameter smaller than that of said chamber tube with a radial circular flange secured within said chamber tube.

13. The apparatus of claim 11, wherein said aroma chamber comprises tube means configured to fit to said air stream nipple, wherein said tube means contains said aroma releasing material.

* * * * *